(12) United States Patent
Koch

(10) Patent No.: US 9,265,592 B2
(45) Date of Patent: Feb. 23, 2016

(54) CLAMPING DEVICE

(75) Inventor: Timo Koch, Gaissau (AT)

(73) Assignee: Armann Girrbach AG, Koblach (AT)

( * ) Notice: Subject to any disclaimer, the term of this patent is extended or adjusted under 35 U.S.C. 154(b) by 200 days.

(21) Appl. No.: 13/823,943

(22) PCT Filed: Jun. 19, 2012

(86) PCT No.: PCT/AT2012/000172
§ 371 (c)(1),
(2), (4) Date: May 31, 2013

(87) PCT Pub. No.: WO2013/020147
PCT Pub. Date: Feb. 14, 2013

(65) Prior Publication Data
US 2013/0244846 A1 Sep. 19, 2013

(30) Foreign Application Priority Data
Aug. 10, 2011 (DE) .......................... 10 2011 109 939

(51) Int. Cl.
*B23Q 3/157* (2006.01)
*A61C 13/00* (2006.01)
(Continued)

(52) U.S. Cl.
CPC ............. *A61C 13/00* (2013.01); *A61C 13/0003* (2013.01); *A61C 13/0022* (2013.01);
(Continued)

(58) Field of Classification Search
CPC ........... B23Q 3/15506; B23Q 3/15546; B23Q 3/15566; B23Q 3/15706; B23Q 1/4809; B23Q 1/4833; B23Q 1/5443; Y10T 409/305824; Y10T 409/308792; Y10T 483/132; Y10T 483/134; Y10T 483/1793; Y10T 483/1795; Y10T 483/1798; Y10T 483/1873

USPC ........... 483/8, 9, 54, 55, 56, 66; 409/168, 221
See application file for complete search history.

(56) References Cited

U.S. PATENT DOCUMENTS

| 3,339,273 A | | 9/1967 | Knosp | |
|---|---|---|---|---|
| 3,760,489 A | * | 9/1973 | Griffith | ............................. 483/9 |
| 4,164,290 A | | 8/1979 | Zankl | |
| 4,615,678 A | | 10/1986 | Moermann et al. | |
| 5,257,199 A | * | 10/1993 | Tsujino et al. | ................. 700/160 |

(Continued)

FOREIGN PATENT DOCUMENTS

| DE | 102009011672 | 7/2010 |
|---|---|---|
| DE | 102009011676 | 7/2010 |

(Continued)

OTHER PUBLICATIONS

EPO English Translation of DE102009011676A1—Evertz et al., "Processing machine machining workpiece, has stationary frame, and work piece holder that is automatically moved in relation to frame for receiving work piece to be machined," Jul. 29, 2010.*

(Continued)

*Primary Examiner* — Erica E Cadugan
*Assistant Examiner* — Michael Vitale
(74) *Attorney, Agent, or Firm* — Volpe and Koenig, P.C.

(57) ABSTRACT

A clamping device (1) for a machine tool (2) for machining at least one dental workpiece (3), wherein the clamping device (1) has at least one workpiece carrier (4) for accommodating the dental workpiece (3) during machining, wherein at least one tool holder (5) for holding at least one, preferably a plurality of cutting tools (6) for machining the dental workpiece (3) is arranged, preferably fixedly, on the workpiece carrier (4), and the workpiece carrier (4) and the tool holder (5) are fastened or fastenable together as one component on a carrier of the clamping device (1) in an exchangeable manner by a fastening device (7) that is non-destructively releasable, preferably without a tool.

15 Claims, 9 Drawing Sheets

(51) Int. Cl.
*B23Q 1/25* (2006.01)
*B23Q 3/06* (2006.01)
*B23Q 3/155* (2006.01)
*B23C 1/02* (2006.01)
*B23Q 11/08* (2006.01)
*B23Q 1/54* (2006.01)

(52) U.S. Cl.
CPC ............... *B23Q 1/25* (2013.01); *B23Q 1/5443* (2013.01); *B23Q 3/06* (2013.01); *B23Q 3/15506* (2013.01); *B23Q 3/15526* (2013.01); *B23Q 3/15706* (2013.01); *A61C 13/0004* (2013.01); *B23C 1/02* (2013.01); *B23Q 1/5406* (2013.01); *B23Q 1/5412* (2013.01); *B23Q 3/15546* (2013.01); *B23Q 11/0891* (2013.01); *Y10T 409/30392* (2015.01); *Y10T 409/305824* (2015.01); *Y10T 483/132* (2015.01); *Y10T 483/17* (2015.01); *Y10T 483/1743* (2015.01); *Y10T 483/1795* (2015.01); *Y10T 483/1873* (2015.01)

(56) References Cited

U.S. PATENT DOCUMENTS

| | | |
|---|---|---|
| 6,799,758 B2 | 10/2004 | Fries |
| 8,333,536 B2 * | 12/2012 | Shih ........................ 409/137 |
| 2004/0121890 A1 * | 6/2004 | Taga et al. ................ 483/54 |
| 2011/0018184 A1 | 1/2011 | Steger |
| 2011/0083307 A1 * | 4/2011 | Shih ........................ 29/26 A |
| 2012/0172185 A1 * | 7/2012 | Yang ........................ 483/13 |

FOREIGN PATENT DOCUMENTS

| | | |
|---|---|---|
| EP | 0160797 | 1/1989 |
| EP | 1321221 | 6/2003 |
| EP | 1765550 | 1/2010 |
| EP | 2305419 | 4/2011 |
| WO | 2009100863 | 8/2009 |

OTHER PUBLICATIONS

R&K CAD/CAM Catalogue, "Organical CAD/CAM, The Dental CAD/CAM—Milling System," Jan. 1, 2010.*

* cited by examiner

CLAMPING DEVICE

BACKGROUND

The present invention relates to a clamping device for a machine tool for machining at least one dental workpiece, wherein the clamping device has at least one workpiece carrier for accommodating the dental workpiece during machining.

Various embodiments of clamping devices of the type in question are known in the prior art. For example, WO 2009/100863 A2 shows a clamping device, in which two rings are arranged pivotably relative to each other, wherein a plate-like workpiece carrier can be fastened in the inner ring and the dental workpiece which is to be machined is held in a circumferentially closed manner in a passage opening in the workpiece carrier.

The various dental workpieces to be machined in the current prior art consist of different materials. This is a first reason why a machine tool for machining such dental workpieces requires not only one tool, but generally a plurality of tools. A second reason for the necessity of using different tools also resides in the different dimensions and accuracy with which work can be carried out with the particular tool. In order to be able to operate the machine tool with different tools for machining the central workpiece, WO 2009/100863 proposes, in FIG. 4, equipping the machine tool with a plurality of tool carrier heads which each carry and drive a tool. However, this is highly complicated.

SUMMARY

It is therefore the object of the invention to provide an alternative solution proposal as to how different tools can be made available to the machine tool simply and rapidly.

According to the invention, this is achieved by a clamping device of the abovementioned type, in which it is provided that at least one tool holder for holding at least one cutting tool, preferably a plurality of cutting tools, for machining the dental workpiece is arranged, preferably fixedly, on the workpiece carrier, and the workpiece carrier and the tool holder are fastened or are fastenable together as one component on a carrier of the clamping device in an exchangeable manner by means of a fastening device which is non-destructively releasable, preferably without a tool.

In other words, it is therefore a basic concept of the invention to integrate the workpiece carrier and the tool holder into a common component which can then be fastened in an exchangeable manner to the carrier of the clamping device and can also be interchanged for a different component, preferably having a workpiece carrier and tool holder. This basic concept of the invention is also based on the idea that certain types of workpiece carriers are generally provided for workpieces consisting of certain materials that have to be machined with a certain set of tools. In the case of the invention, this set of tools can be held on the tool holder which forms a common component together with the workpiece carrier. This has the result that, upon installation of a certain workpiece carrier on the carrier of the clamping device, the correct set of tools held on the tool holder is also immediately available to the machine tool. It is particularly advantageous in this connection if the fastening device is operable and/or reachable by the end user of the clamping device. Within this context, the fastening device should be arranged in such a manner that the end user of the clamping device can operate said fastening device without having to dismantle or disassemble the clamping device or the entire machine tool.

The fastening device which is non-destructively releasable, preferably without a tool, may be, for example, a latching connection and/or a rapid clamping system. Other examples of suitable fastening devices include appropriately retentive plug-in systems, quarter turn fastenings or the like. In this context, the term "without a tool" means that the actuation of the fastening device for release and connection of the common component which has the workpiece carrier and the tool holder from and to the carrier is possible directly by hand preferably without using additional auxiliary means, such as, for example, screwdrivers or wrenches. However, within the context of the invention, the actuation of the fastening device by means of a tool can also be provided. The term of non-destructive releasability should be interpreted to the effect that the fastening device is configured for multiple release and re-connection. The fastening and the release can therefore be carried out virtually as frequently as desired without the fastening device or other components being destroyed.

Advantages of the invention are provided in that tools and workpiece holders which are matched to the particular requirements and are held on the tool holder are provided and it is thereby also ensured that both the workpiece carrier with the workpiece and also the tools can be arranged in a precisely known and defined position for the machine tool. This permits both the positionally correct positioning of the dental workpieces which are to be machined in the clamping device and therefore also in the machine tool, and also the possibility of bringing the tools for the machine tool, and in particular the tool carrier head thereof, into an approachable position.

It should basically be emphasized that clamping devices according to the invention and also machine tools can be used for machining a very wide variety of dental workpieces. These may be blanks or initial products, for example ceramic, metal or zirconium blocks. However, semi-finished products, such as already partially machined prostheses, partial prostheses or the like may also be further machined as dental workpieces. The dental workpieces may also be, however, auxiliary frameworks or carriers which are required in the production of dental prostheses or partial prostheses.

The term "machining" is known per se. It primarily involves milling and/or drilling operations. However, other types of machining with corresponding tools can also be carried out.

The workpiece carrier is the component which is provided for accommodating the dental workpiece to be machined. The dental workpiece can be held on or fastened to the workpiece carrier directly or indirectly, for example with the interconnection of a frame. In preferred embodiments of the invention, the workpiece carrier is mounted together with the tool holder on the carrier so as to be rotatable, preferably by motor, about a, preferably first, axis. In the case of the carrier, provision may be made for said carrier to be a supporting arm which is mounted so as to be rotatable, preferably by motor, about a, preferably second axis which is different from the first axis. Within the context of easy accessibility to the dental workpiece to be machined, it is advantageously provided that the workpiece carrier and the tool holder are mounted together laterally on the carrying arm.

The tool holder is advantageously a type of store for tools which are not immediately required during the machining operation currently carried out. Tools may in principle be all tools which are suitable for machining the dental workpiece. Milling or drilling heads are primarily involved in this case. The tool holder advantageously has one or more tool holding fixtures for holding the tools not immediately required. These are predetermined or defined spaces on the tool holder, at which certain tools can be deposited in a defined manner.

It is advantageous if the cutting tool is held releasably or is accommodated on a tool holding fixture of the tool holder, or the cutting tools are held releasably or are accommodated on tool holding fixtures of the tool holder, preferably magnetically or by means of a latching connection. As an alternative to the magnet and to the latching connection, other form-fitting or frictional types of fastening the tools in the tool holding fixtures of the tool holder are also conceivable. The type of fastening is intended, firstly, to hold the tool in an appropriately secure manner on the tool holder but, secondly, is also intended not to stand in the way of removing a tool from the tool holder by means of the tool carrier head of the machine tool.

In contrast to the tool holder which bears the tools not required during the current machining operation, the tool carrier head is that component of a machine tool which receives, drives and positions the cutting tool during the machining of the workpiece. The tool carrier head is advantageously movable in at least one, preferably two, particularly preferably three spatial directions such that it is able, at different locations, to approach the dental workpiece, which is held in the workpiece carrier of the clamping device and is to be machined, with the tool.

In order for the tool carrier head to be able in an automated manner to remove tools from the tool holder, to reinsert them there again and to carry out a change of tools, it is advantageous if the tool holder has one or more tool holding fixtures for accommodating one cutting tool each, and the clamping device has an identifying device for checking whether a cutting tool and/or which cutting tool are/is present in the tool holding fixture or respective tool holding fixtures. Depending on the embodiment, the identifying device can therefore firstly identify whether a tool is or is not present at all at the corresponding location or at the corresponding tool holding fixture of the tool holder. However, particularly preferred embodiments can also identify which type of tool is present at the corresponding location or in the corresponding tool holding fixture of the tool holder. The modes of operation of suitable identifying devices are known per se in the prior art. They may be, for example, reading devices for electric, electromagnetic, magnetic, mechanical or optically readable codes which are then advantageously fixed on each tool for individualization purposes. Reading devices for transponders, RFIDs, barcodes, microchips and the like should also be mentioned in this connection.

In addition to the clamping device per se, the invention also relates to a machine tool for machining at least one dental workpiece, comprising at least one clamping device according to the invention. It is advantageously provided in such a machine tool that it has a housing with a machining cavity which is closable, preferably completely, during the machining of the dental workpiece, wherein the fastening device is arranged in the machining cavity preferably so as to be operable and/or reachable by the end user of the clamping device. Furthermore, it is advantageously provided that, in addition to the clamping device, the machining device also has at least one tool carrier head which accommodates and drives at least one of the cutting tools for machining the workpiece, wherein, for changing a tool, the tool carrier head can deliver one cutting tool to the tool holder and can receive another cutting tool from the tool holder. Furthermore, it is advantageously provided that the machine tool is a computer-controlled machine tool. In these embodiments, the rotation of the workpiece carrier about the first axis and the rotation of the carrying arm about the second axis and optionally also the movement of the tool carrier head and/or of the tool can advantageously be carried out under computer control. A corresponding control computer can be integrated into the machine tool or can be connected to said machine tool in order to activate the latter.

BRIEF DESCRIPTION OF THE DRAWINGS

Further features and details of preferred embodiments of the invention are explained in the description of the figures below with reference to different figures relating to an exemplary embodiment according to the invention of a machine tool comprising a corresponding clamping device. In the figures.

DETAILED DESCRIPTION OF THE PREFERRED EMBODIMENTS

Figure 4:
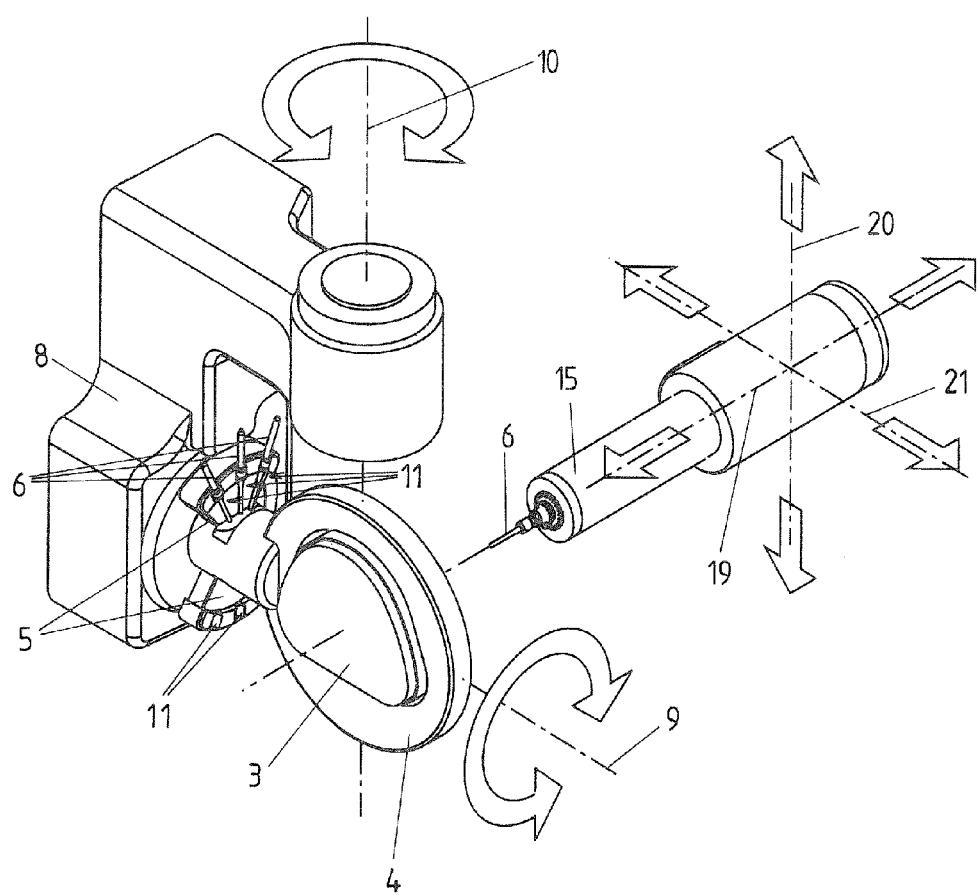
FIG. 4 shows the clamping device according to the invention of said machine tool together with the tool carrier head of said machine tool with the other components of the machine tool being omitted.

The machine tool 2 illustrated in the figures has a housing 13 with a machining cavity 14 arranged therein. The dental workpiece 3 to be machined is arranged in the machining cavity 14 during machining. This workpiece is held by means of the clamping device 1 in the machining cavity 14 during machining and can also be positioned by means of the clamping device 1 for machining in defined positions relative to the tool carrier head 15 or to the tool 6 specifically arranged thereon for the particular machining step. The dental workpiece 3 (not illustrated in FIG. 1) which is to be machined is arranged on the workpiece carrier 4 directly or indirectly, for example by the interconnection of a frame surrounding the dental workpiece. According to the invention, the workpiece carrier 4 and the tool holder 5 form a common component which is fastened or is fastenable on a carrier of the clamping device 1 in an exchangeable manner by means of the fastening device 7 which is non-destructively releasable, preferably without a tool. In the exemplary embodiment shown, the carrier of the clamping device 1 is the carrying arm 8. The component formed by the workpiece carrier 4 and the tool holder 5 is mounted on said carrying arm so as to be rotatable, preferably by motor, about a preferably first axis 9. The carrier which is embodied here as a carrying arm 8 is, in turn, advantageously mounted so as to be rotatable, preferably by motor, about a, preferably second axis 10 which is different from the first axis 9. FIG. 4, with omission of the other components of the machine tool 2, illustrates the possible directions of movement and therefore the degrees of freedom of the clamping device 1 and of the tool carrier head 15. The carrier or carrying arm 8 is rotatable, preferably exclusively, about the second axis 10. The curved double arrow illustrates the two possible, mutually opposed directions of rotation of the carrying arm 8. The angle of rotation may be 360° and more. However, it is equally possible to restrict said angle of rotation about the second axis 10 to a smaller angular range. The rotation about the axis 10 is advantageously the single possibility of movement of the carrying arm 8. The workpiece carrier 4 which, in FIG. 4, carries a dental workpiece 3 in the form of a blank is mounted on the carrying arm 8 so as to be rotatable about the first axis 9. The double arrow in turn shows the two opposed directions of rotation about the axis of rotation 9. By means of the single-piece formation of the workpiece carrier 4 and tool holder 5 as a common component, the tool holder 5 and workpiece carrier 4 are rotated together about the axis 9.

FIG. 4 illustrates two free tool holding fixtures 11, i.e. spaces for arranging a tool 6 on the tool holder 5, and three tool holding fixtures 11 of the tool holder 5 that are occupied by means of tools 6. In this case, the tools 6 which are preferably in the form of milling or drilling heads can be selected in such a manner that precisely those tools 6 which are suitable and are required for machining the dental workpiece 3 fastened in the workpiece carrier 4 are held on the respective tool holder 5. One of the tools 6 is mounted on the tool carrier head 15 for the machining operation taking place at that particular instant. The tools 6 are advantageously exchanged in an automated manner by the tool carrier head 15 retrieving the corresponding tool 6 from the tool holder 5. In this case, the tool holder 5 can be rotated together with the workpiece carrier 4 into a position such that the tool 6 required in each case at the particular instant can be picked up by the tool carrier head 15. The same applies to the delivery of a tool 6 that is no longer immediately required to the corresponding tool holding fixture 11 of the tool holder 5. The tools 6 are advantageously picked up and deposited and therefore also changed in a fully automated manner at the tool carrier head 15. So that the controller system of the machine tool or clamping device 1 identifies with a tool 6 and/or which tool 6 is arranged on the respective tool holding fixture 11, the identifying device 12 already mentioned at the beginning is advantageously provided. The latter, as already explained at the beginning, can operate in order to identify the presence and/or the type of tool 6 arranged in each case on a tool holding fixture 11.

It is also illustrated in FIG. 4 that, as preferably provided, the tool carrier head 15 in this exemplary embodiment is movable in three directions 19, 20 and 21 orthogonal with respect to one another. The respective arrows indicate the possible directions of movement forwards, back, laterally, vertically and downward. With the total of five axes of movement illustrated in FIG. 4, it is possible to machine a dental workpiece 3 at the desired angle at any location. Within the context of easy accessibility of the workpiece 6 fastened to the workpiece carrier 4, it is advantageous if the workpiece carrier 4 is mounted, preferably laterally, on the carrying arm 8 of the clamping device 1 so as to be rotatable about the first axis 9 and the carrying arm 8 is mounted so as to be rotatable about the second axis 10. In this case, the respective rotational movements about the respective axes 9 and 10 can be the single rotational movement possibilities of the carrying arm 8 and tool carrier 4. Provision can be made for the rotatable mounting of the workpiece carrier 4, preferably laterally, on the carrying arm 8 to be the sole carrying fastening of the workpiece carrier 4. In other words, provision can be made for the workpiece carrier 4 to be mounted on the carrying arm 8 exclusively on one side and/or only via a single connection. It is advantageous in this connection if the carrying arm 8 is designed to be bent and/or angled or, as realized here, L-shaped per se. As realized in this exemplary embodiment, the workpiece carrier 4 can be mounted, preferably laterally, on the carrying arm 8, in a first end region thereof, so as to be rotatable about the first axis 9. Furthermore, the carrying arm 8 can be mounted, in a second end region of the carrying arm 8, so as to be rotatable about the second axis 10, for example on the housing 13 of the machine tool 2. As also realized here, the first axis 9 and/or the second axis 10 and the imaginary extensions thereof can run through the workpiece accommodating region of the workpiece carrier 4 that is provided for accommodating the dental workpiece 3.

Returning to FIGS. 1 to 3, it should be pointed out that the machining cavity 14, in which, advantageously, both the clamping device 1 and the tool carrier head 15 are arranged movably, can advantageously be closed during the machining of the dental workpiece 3 to be machined. This may involve a dust- and/or liquid-proof type of closure. In the exemplary embodiment shown, the hingeable closure flap 16 is provided for this closure option. The required sealing can be obtained via corresponding sealing rings, which are known in the prior art, and the like. For the sake of completeness, it is pointed out that the movement of the clamping device 1 and of the tool carrier head 15 is advantageously carried out by motor or by motor operation. The activation is advantageously undertaken by means of computer. As already explained at the beginning, the machine tool 2 is advantageously a computer-controlled machine tool.

Figure 1:
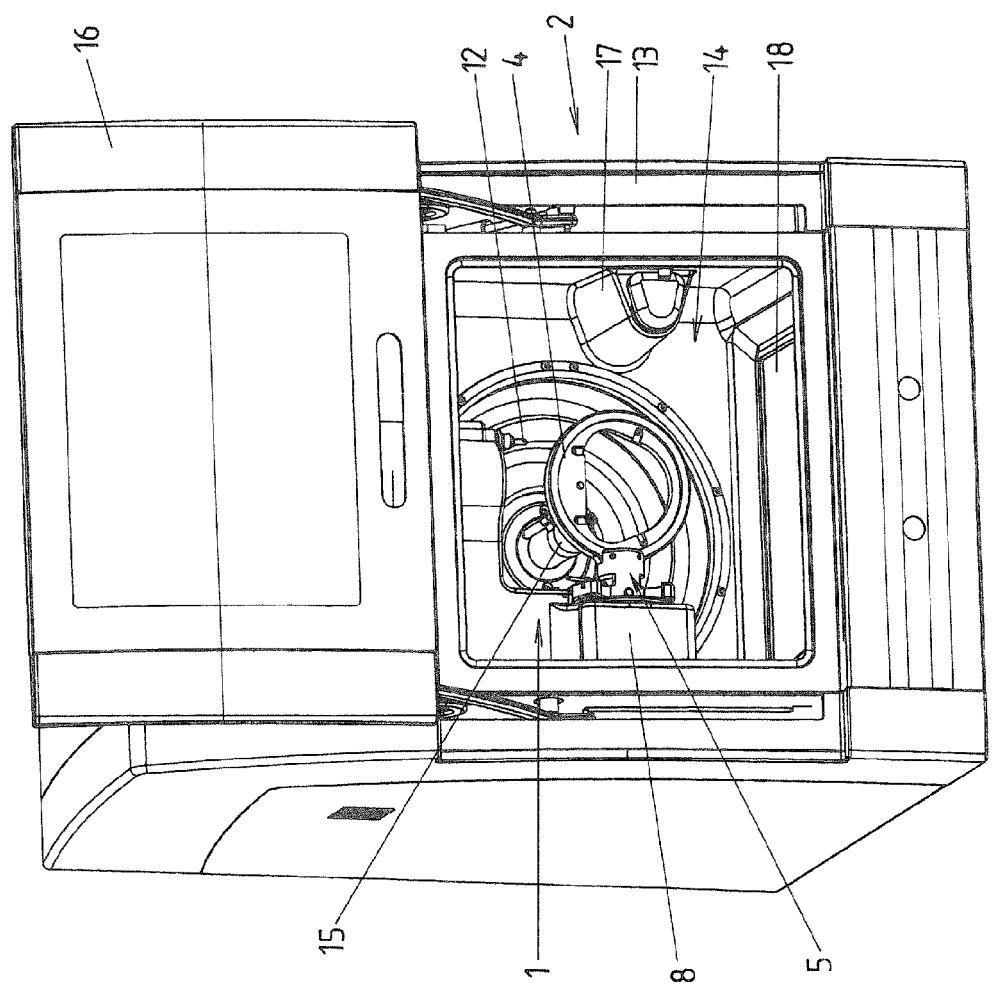
FIG. 1 shows a first perspective view of a machine tool according to the invention for machining at least one dental workpiece with a corresponding clamping device according to the invention.
Figure 2:
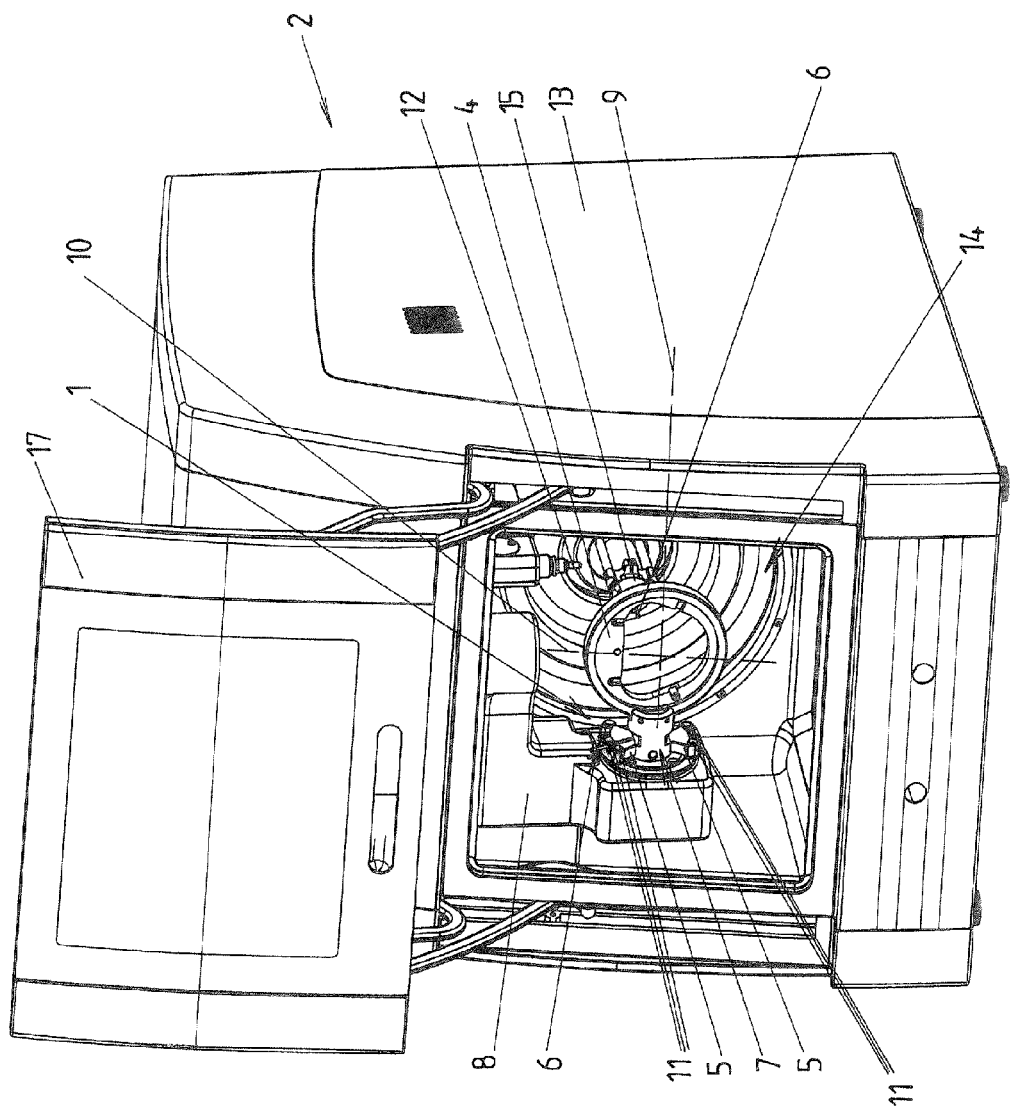
FIG. 2 shows a second perspective view of said machine tool.
Figure 3:
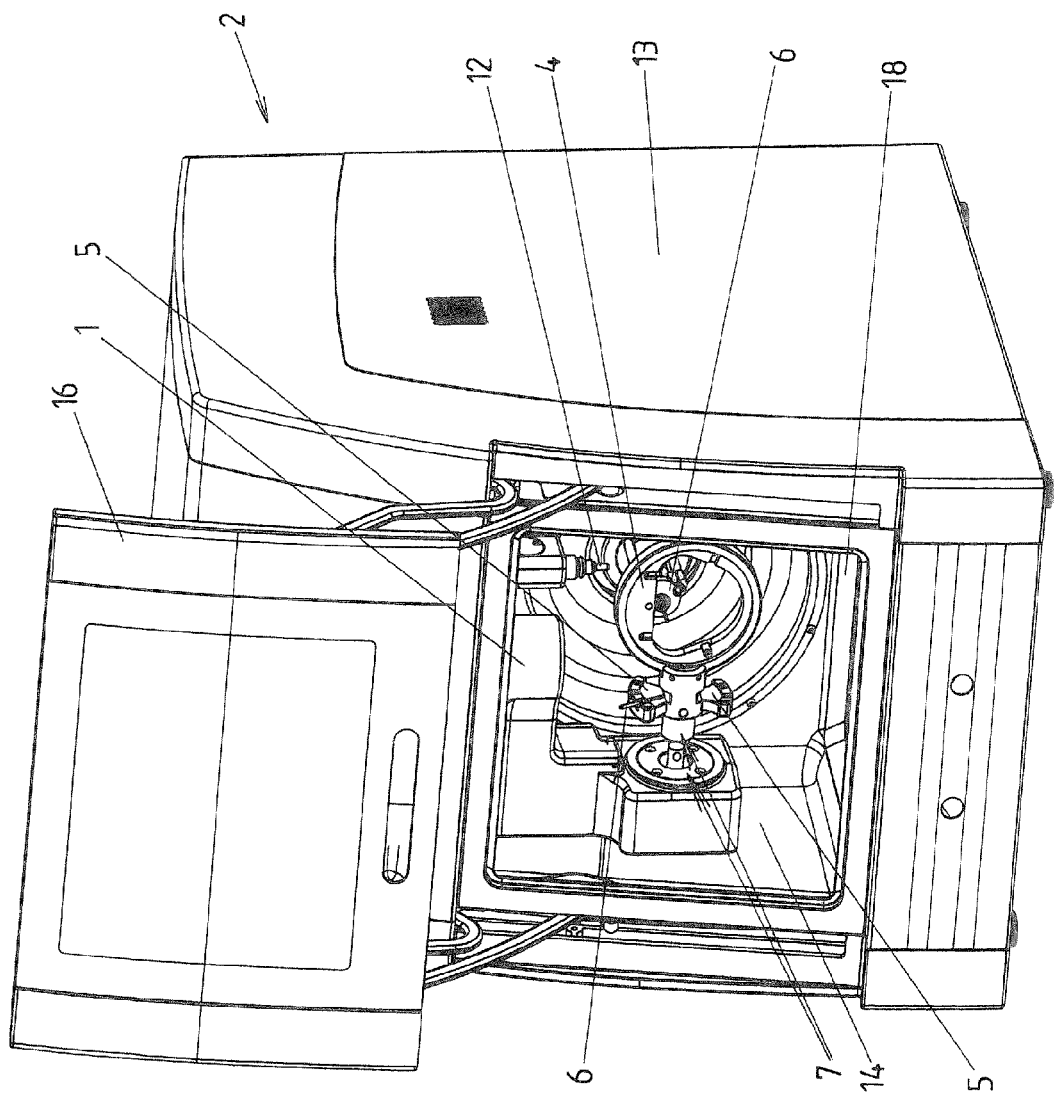
FIG. 3 shows a view which is otherwise analogous to FIG. 2, but in which the component forming the workpiece carrier and the tool holder has been released from the carrier of the clamping device.
Figure 5:
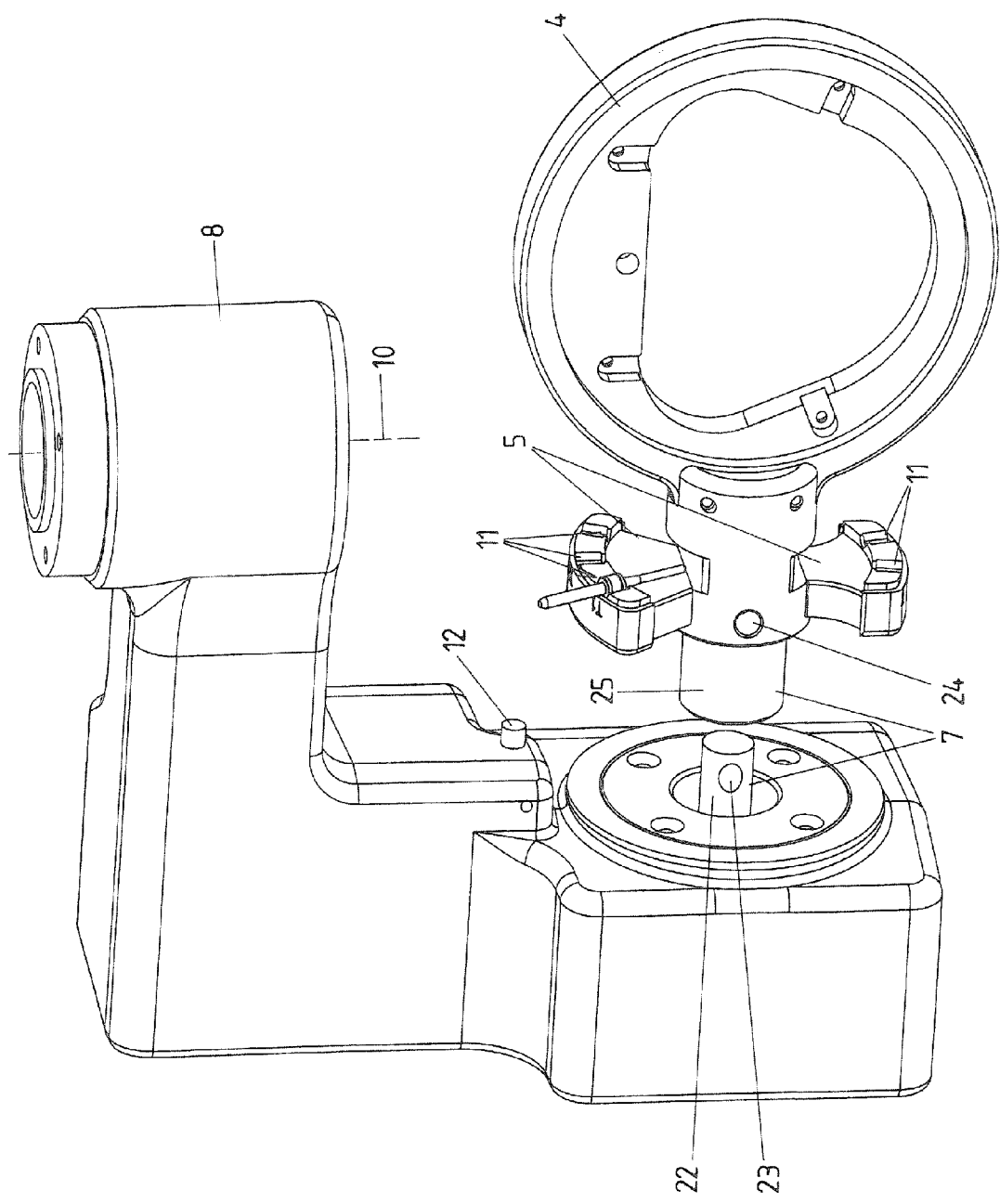
FIG. 5 shows a view of the clamping device according to the invention, wherein the component forming the tool carrier and the tool holder has been released from the carrying arm.

In FIGS. 1 and 2, the common component which comprises both the workpiece carrier 4 and the tool holder 5 is fastened to the carrying arm 8 by means of the fastening device 7. This is the operating position in which said common component is rotatable about the axis 9 and, together with the carrying arm 8, is rotatable about the axis 10. If a different workpiece is then intended to be machined, the workpiece carrier 4 and the tool holder 5 are removed together from the carrying arm 8, by release of the fastening device 7, which is non-destructively releasable, preferably without a tool, and replaced by another unit, for example consisting of another workpiece carrier 4 with a corresponding tool holder 5 and tools 6 correspondingly arranged thereon. FIG. 3 and FIG. 5 show, once again on an enlarged scale, the component consisting of the workpiece carrier 4 and tool holder 5 released from the carrying arm 8. In the exemplary embodiment shown, as can be seen particularly readily in FIGS. 3 and 5, the fastening device 7 which is non-destructively releasable is formed by a bolt 22, which is rotatable about the axis 9, on the carrying arm 8 and a matching bolt receptacle 25 on the common component of the workpiece carrier 4 and the tool holder 5 and also by a connecting bolt (not shown here). If the component consisting of the workpiece carrier 4 and tool holder 5 is plugged to a sufficient distance onto the carrying arm 8, the connecting bolt can be plugged through the plug-through openings 23 and 24 into bolt 22 and bolt receptacle 25 or screwed therein, thus achieving the required locking for the machining. The connecting bolt can be in the form of, for example, a conical bolt with or without a thread. For the actuation, it can have a connecting piece, for example a screwdriver slot, a polygonal stub or a hexagon socket, wherein a tool, for example a screwdriver, a wrench, a hexagon key or a torque wrench, can be fitted on the connecting piece for actuation purposes. Within the context of a tool-free actuation of the fastening device 7, the connecting bolt may also, however, be provided with a gripping element which is actuable directly by hand, i.e. without a tool.

If the common component is intended to be replaced by a different common component with a different workpiece carrier 4 and tool holder 5, the connecting bolt is to be pulled out, and the common component pulled off from the carrying arm 8 in order then to fasten a different common component in a corresponding manner to the carrying arm 8.

Figure 6:
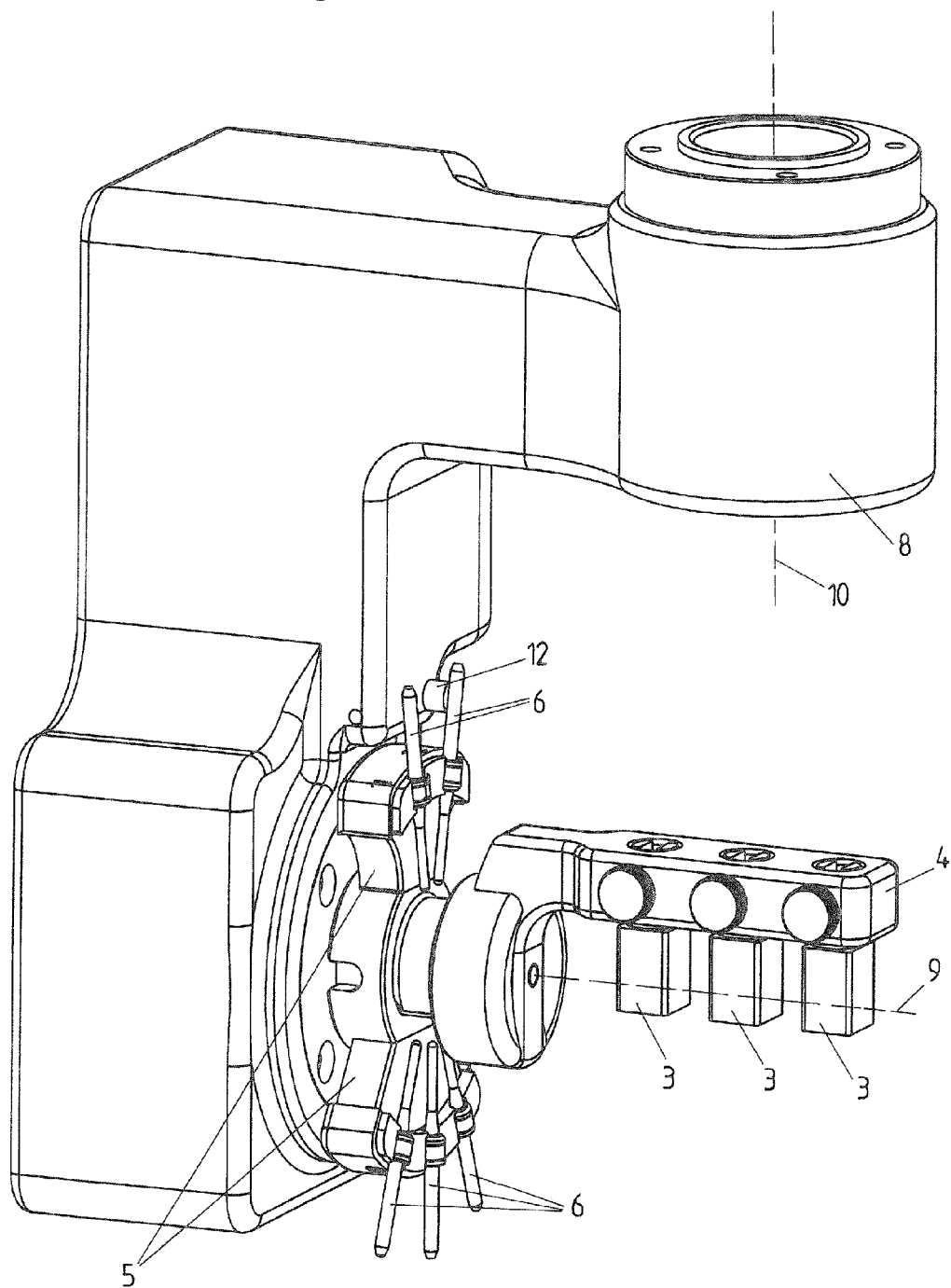
FIG. 6 shows the clamping device to which a different tool consisting of the workpiece carrier and tool holder is fastened by means of the non-destructively releasable fastening device.

FIG. 6 shows, by way of example, a different component with a different tool carrier 4 and a different tool holder 5 with tools 6 correspondingly matched to the dental workpieces 3 to be machined here. As illustrated by a comparison of FIGS. 5 and 6, the shaping of the workpiece carrier 4 has scarcely any limits per se. It may be a workpiece carrier 4 which completely encloses or engages around the dental workpiece 3 in a plane, as in FIG. 5, but, for example, also workpiece carriers 4 only laterally holding the workpieces 3, as in FIG. 6. Other embodiments, such as C-shaped bows or the like are also conceivable for the workpiece carriers 4.

Figure 7:
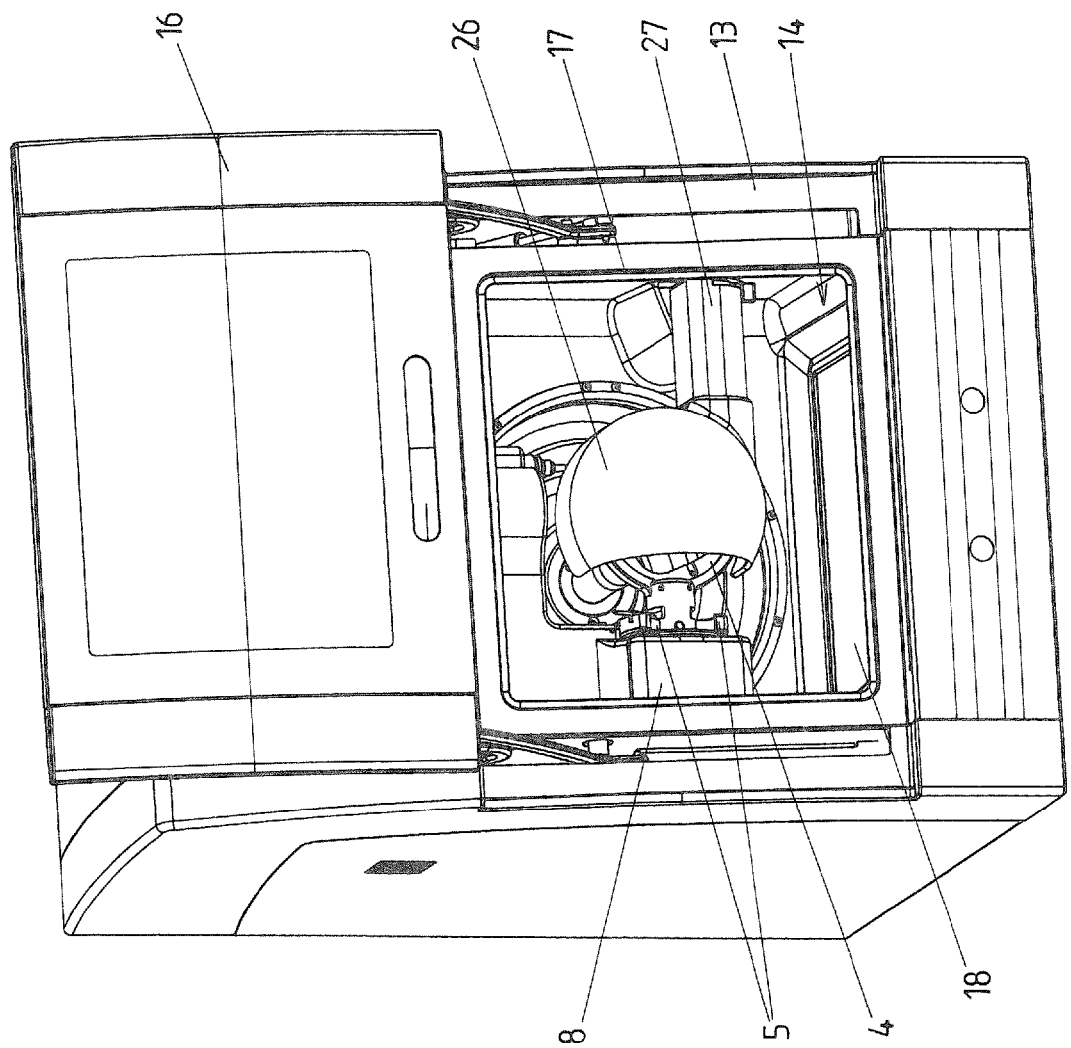
FIG. 7 shows the machine tool with a suction bell provided for dry machining.
Figure 8:
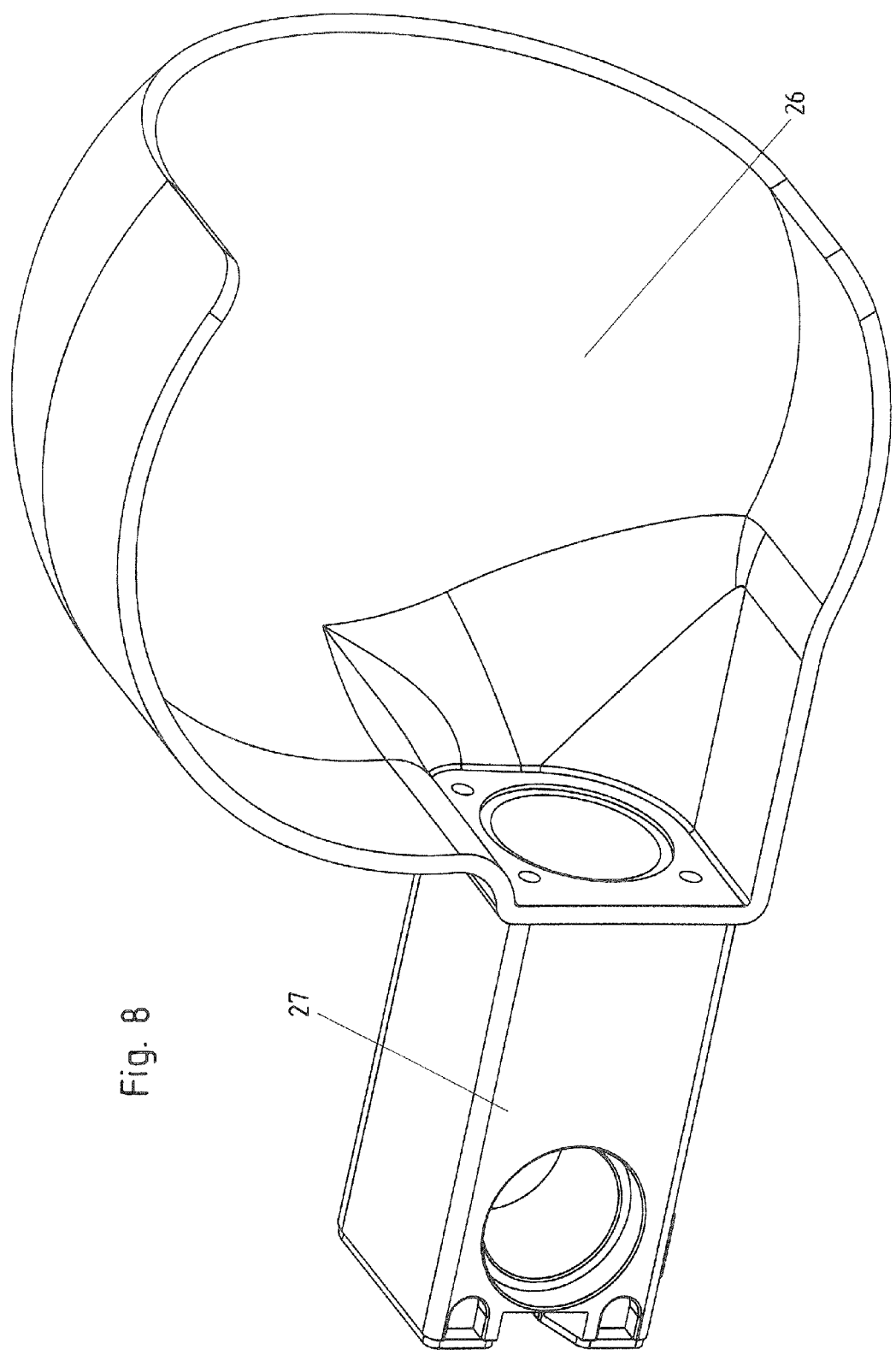
FIG. 8 shows the suction bell from FIG. 7 in an enlarged illustration.

Machine tools 2 designed according to the invention can be provided for the dry machining of dental workpieces 3, but also for the wet machining of the dental workpieces 3. The exemplary embodiment shown involves a preferred embodiment which is suitable both for the dry and for the wet machining of dental workpieces 3. For the dry machining, the machine tool 2 of the exemplary embodiment shown has a suction means 17. For the dry machining of the dental workpiece, the suction bell 26, which is illustrated mounted in FIG. 7 and released in FIG. 8, can be connected to said suction means. This suction bell is advantageously fastenable and arrangeable releasably on the air suction means 17 in the machining cavity 14. In the exemplary embodiment shown, the suction bell 26 is connected to the suction means 17 via the connecting stub 27. In addition to the described suction means, air nozzles can also be provided, for example on the tool carrier head 15, for the dry machining, with which air nozzles the tool 6 used for the particular machining step can be cooled and/or with which that region of the dental workpiece 3 which has just been machined can be blown free such that dust and chips produced during machining are blown off the workpiece 3 being machined and are sucked off by the suction means. Of course, the air nozzles may also be arranged separately, i.e. not directly on the tool carrier head 15, and are not illustrated here.

For the wet machining, the machine tool 2 has a coolant circuit, which is advantageously formed in a self-contained manner, for a corresponding cooling liquid. Any coolant known and suitable in the prior art can be used here. For the transport of the coolant in the coolant circuit, pumps and pipes which are known per se are used. It is advantageous if, via corresponding nozzles, in turn preferably arranged on the tool carrier head 15 or also in another manner, the coolant or the rinsing liquid is sprayed onto the workpiece 3 being machined and/or onto the tool 6 used for the machining operation at the particular instant. In the exemplary embodiment shown, the catching shell 18 is provided for catching the coolant or rinsing means which is, in turn, then pumped out of said catching shell. Both for the dry and the wet machining, corresponding filters can be provided in order to separate off the chips and solid particles abraded by the machining from the coolant or rinsing means circuit or from the sucked-off air.

Figure 9:
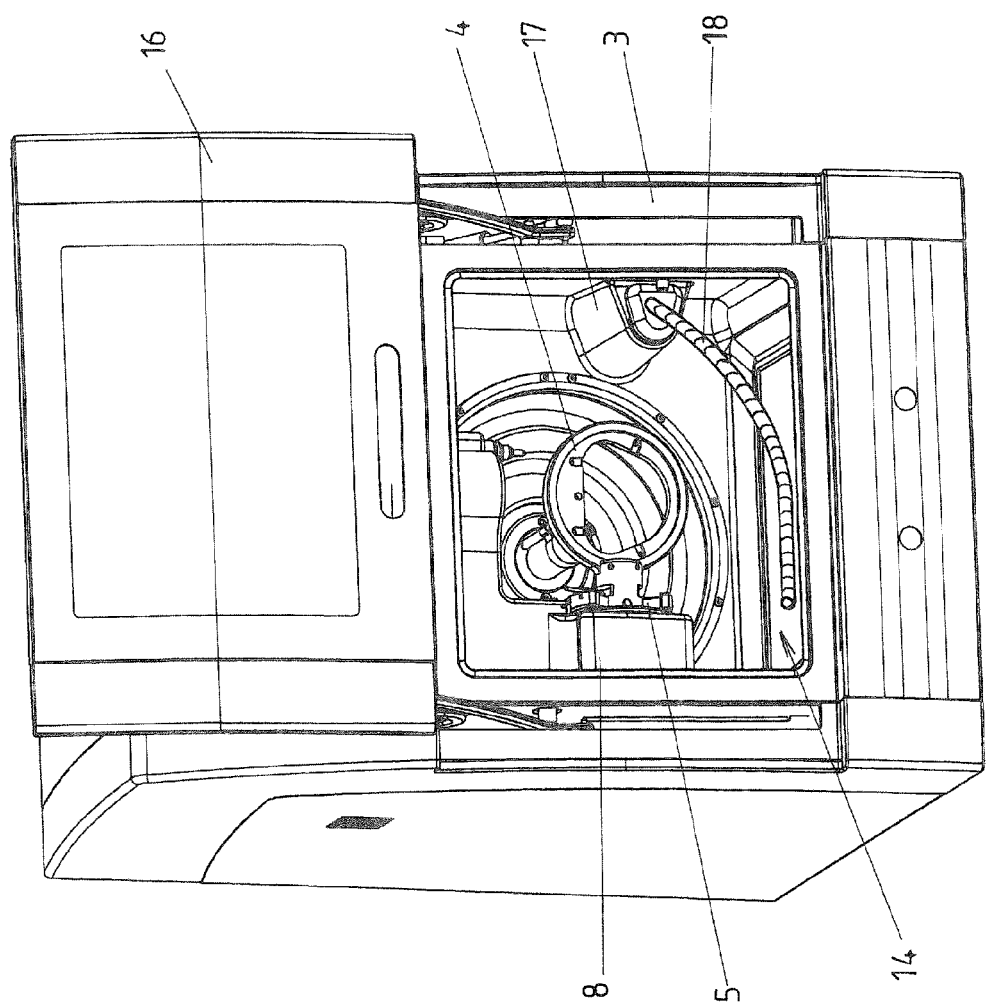
FIG. 9 shows the machine tool of the exemplary embodiment with a suction tube for cleaning in particular the machining cavity before and/or after the machining of the dental workpiece.

In order to be able to clean the machining cavity 14 and/or all of the components, arranged therein, of the clamping device 1 and/or of the machine tool 2 before, during or after the machining operation, preferred embodiments make provision, as shown by way of example in FIG. 9, to be able to connect a suction tube 18 to the air suction means 17. This suction tube 18 is advantageously designed to be of such a length and to be flexible that it can also be used as a type of vacuum cleaner in the machining cavity 14 and optionally also outside the latter. The tube 18 can advantageously be fastened, like the suction bell 26, releasably to the air suction means 17, preferably without a tool. Clamping, latching or other connections of a suitable type are preferably provided here.

LEGEND FOR THE REFERENCE NUMBERS

1 Clamping device
2 Machine tool
3 Dental workpiece
4 Workpiece carrier
5 Tool holder
6 Tool
7 Fastening device
8 Carrying arm
9 First axis
10 Second axis
11 Tool holding fixture
12 Identifying device
13 Housing
14 Machining cavity
15 Tool carrier head
16 Closure flap
17 Air suction means
18 Catching shell
19 Movement device
20 Movement device
21 Movement device
22 Bolt
23 Plug-through opening
24 Plug-through opening
25 Bolt receptacle
26 Suction bell
27 Connecting stub
28 Suction tube

The invention claimed is:

1. A clamping device for a machine tool for machining at least one dental workpiece, the clamping device comprising at least one workpiece carrier for accommodating the dental workpiece during machining, at least one tool holder for holding at least one cutting tool for machining the dental workpiece is arranged on the at least one workpiece carrier, and the at least one workpiece carrier and the at least one tool holder are fastened or are fastenable together as one component, and said one component is connected to a carrier of the clamping device in an exchangeable manner by a fastening device which is non-destructively releasable.

2. The clamping device as claimed in claim 1, wherein the fastening device is at least one of operable or reachable by an end user of the clamping device.

3. The clamping device as claimed in claim 1, wherein the one component is mounted on the carrier of the clamping device so as to be rotatable about a first axis.

4. The clamping device as claimed in claim 3, wherein the carrier of the clamping device comprises a carrying arm which is mounted so as to be rotatable, about a second axis which is different from the first axis.

5. The clamping device as claimed in claim 4, wherein the one component is mounted laterally to a side surface of the carrying arm.

6. The clamping device as claimed in claim 4, wherein the carrying arm which is mounted so as to be rotatable by a second motor about the second axis.

7. The clamping device as claimed in claim 3, wherein the one component is mounted so as to be rotatable by a first motor about the first axis.

8. The clamping device as claimed in claim 1, wherein the at least one cutting tool is held releasably or is accommodated on a tool holding fixture of the at least one tool holder.

9. The clamping device as claimed in claim 1, wherein the at least one tool holder has one or more tool holding fixtures, each for accommodating a respective cutting tool, and the clamping device has an identifying device for checking at least one of whether the at least one cutting tool or which of the respective cutting tools are present in or on the one or more tool holding fixtures.

10. A machine tool for machining at least one dental workpiece, comprising at least one clamping device as claimed in claim 1.

11. The machine tool as claimed in claim 10, further comprising a housing with a machining cavity which is closable during the machining of the dental workpiece, wherein the fastening device is arranged in the machining cavity so as to be at least one of operable or reachable by an end user of the clamping device.

12. The machine tool as claimed in claim 10, further comprising at least one tool carrier head which accommodates and drives the at least one cutting tool for machining the dental workpiece, wherein during a tool change, the at least one tool carrier head delivers the at least one cutting tool to the at least one tool holder and receives a different cutting tool from the at least one tool holder.

13. The clamping device as claimed in claim 1, wherein the at least one tool holder holds a plurality of cutting tools.

14. The clamping device as claimed in claim 1, wherein the at least one tool holder is arranged fixedly on the workpiece carrier.

15. The clamping device as claimed in claim 1, wherein the at least one workpiece carrier and the at least one tool holder are fastened or are fastenable together as the one component on the carrier of the clamping device in an exchangeable manner by the fastening device which is non-destructively releasable without a tool.

* * * * *